United States Patent [19]

Mesek et al.

[11] 3,965,904
[45] June 29, 1976

[54] DISPOSABLE DIAPER

[75] Inventors: Frederick K. Mesek, Downers Grove; Virginia L. Repke, Oak Forest, both of Ill.

[73] Assignee: Johnson & Johnson, New Brunswick, N.J.

[22] Filed: Mar. 18, 1975

[21] Appl. No.: 559,624

[52] U.S. Cl.................................. 128/284; 128/287; 128/290 R
[51] Int. Cl.²................................................ A61F 13/16
[58] Field of Search.............. 128/284, 287, 290 R, 128/290 P

[56] References Cited
UNITED STATES PATENTS

| | | | |
|---|---|---|---|
| 3,768,480 | 10/1973 | Mesek | 128/287 |
| 3,779,246 | 12/1973 | Mesek | 128/287 |
| 3,828,783 | 8/1974 | Kennette | 128/284 |
| 3,838,694 | 10/1974 | Mesek | 128/287 |
| 3,848,598 | 11/1974 | Mesek | 128/287 |

*Primary Examiner*—Aldrich F. Medbery

[57] ABSTRACT

A disposable multi-layer diaper of high absorptive capacity is provided which comprises as a first layer, a porous facing web to be brought into contact with an infant's skin. A second layer, in juxtaposition to the facing layer, is a highly porous, loosely compacted cellulosic batt having greater wettability than that of the facing web. The batt is slightly narrower than the facing layer to provide exposed side portions of the facing layer outwardly of the side edges of the batt. A third layer integral with the second is a continuous, paper-like, densified highly compacted layer of the same cellulosic material as the second layer but of substantially smaller average pore size. The densified layer is bounded by transverse linear areas near the ends of the batt in which areas the densified layer is thickened. The final layer is an impervious backing sheet that is substantially coextensive with the facing layer and which is adhered to the densified layer.

In a preferred embodiment, the densified layer is thickened longitudinally (as well as in the transverse linear areas) in selected areas to provide an increased volumetric flow capacity for rapidly drawing fluid away from an initially wetted area and directing it to areas of the densified layer remote from the wetted area.

17 Claims, 10 Drawing Figures

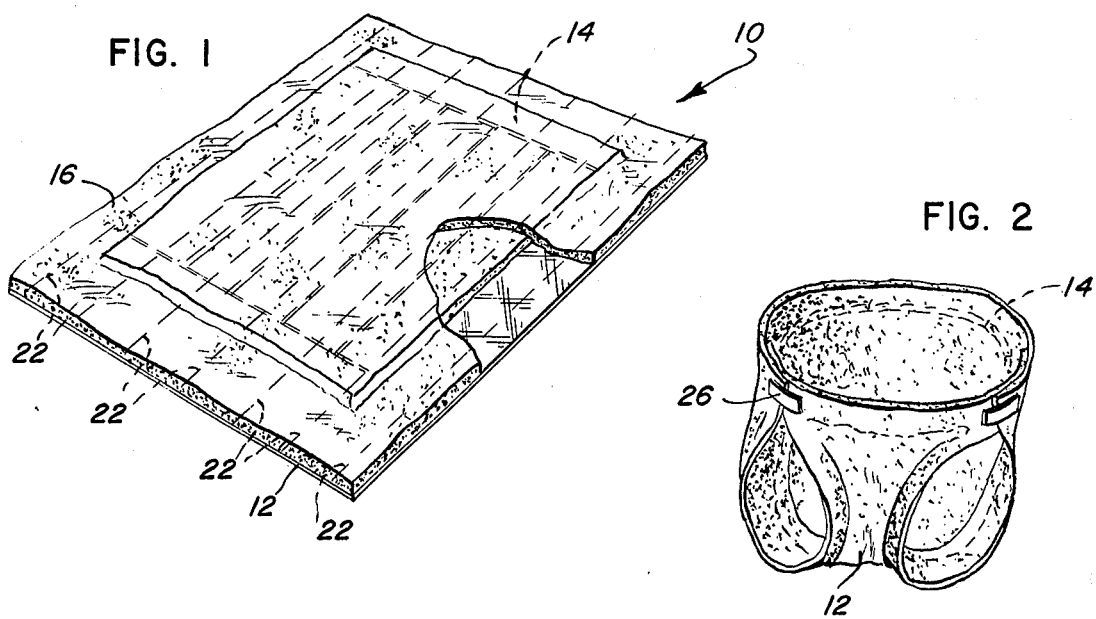
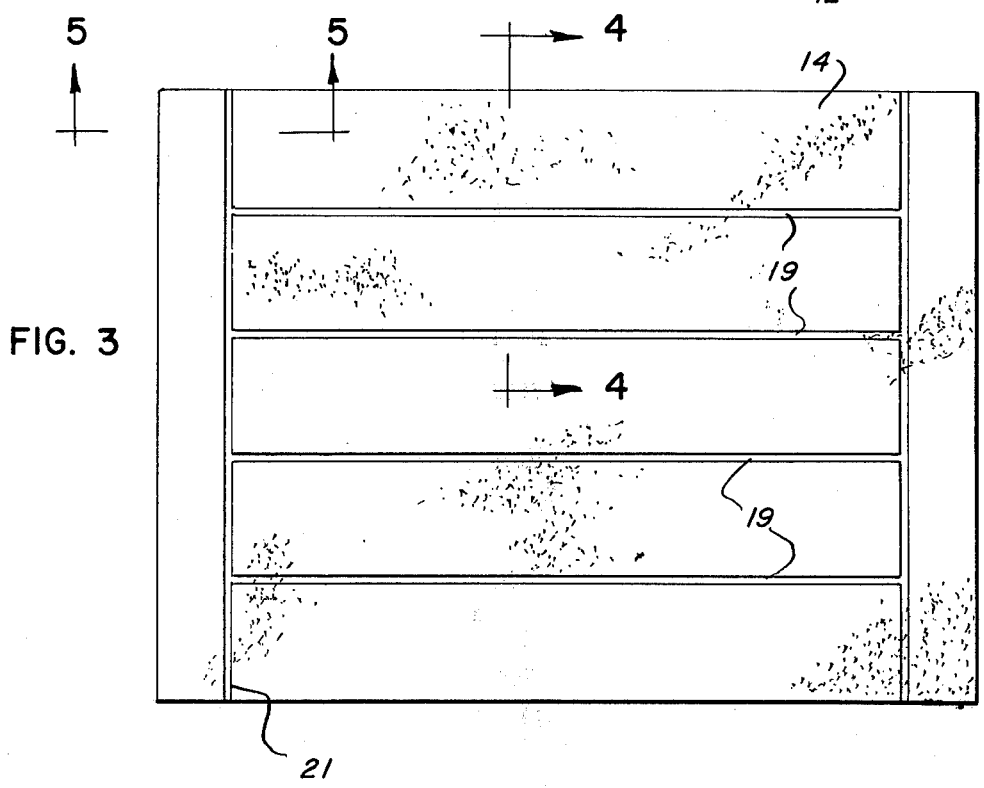
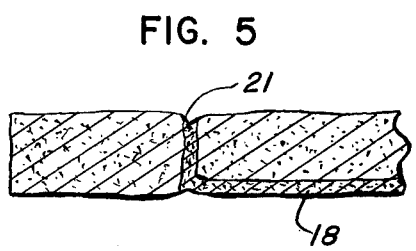
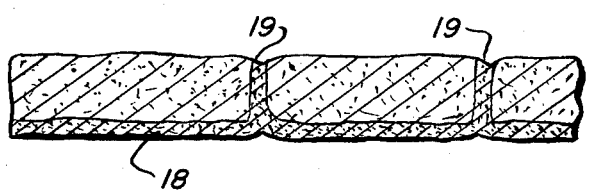

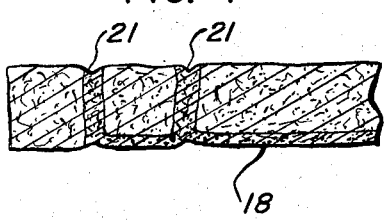
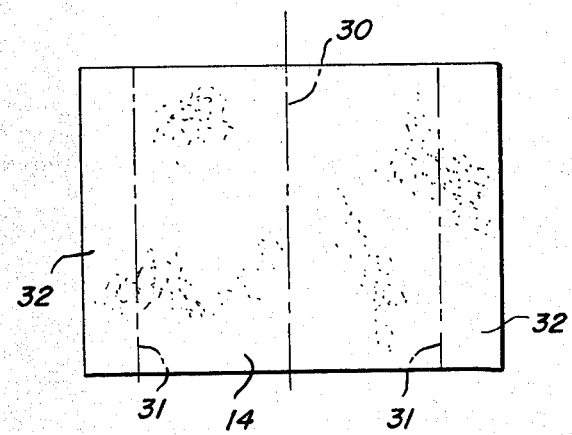
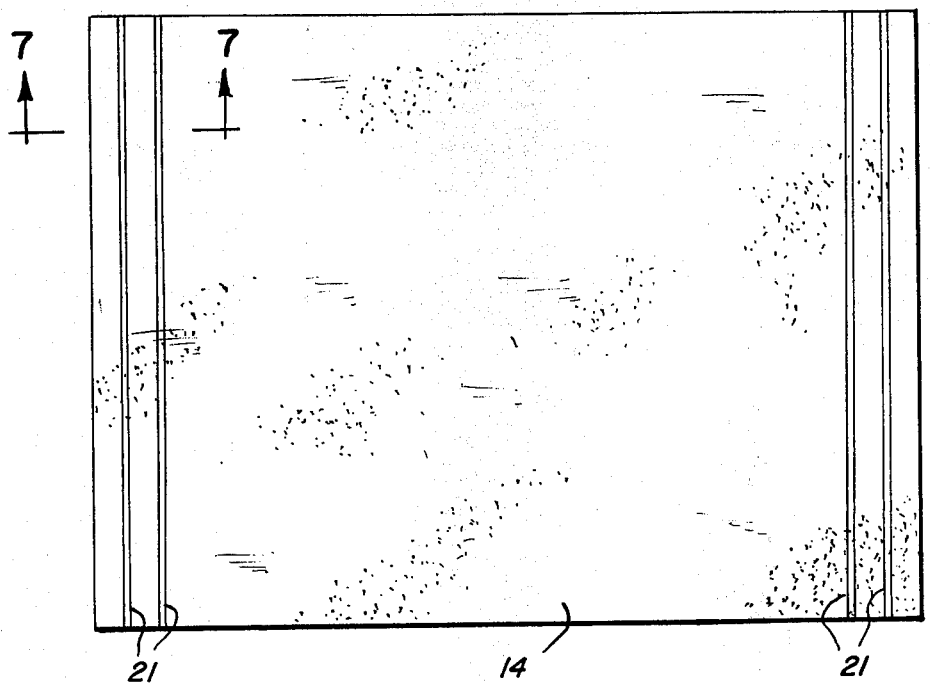

DISPOSABLE DIAPER

BACKGROUND OF THE INVENTION

Disposable diapers have met with increased commerical acceptance in recent years primarily because of their convenience, as opposed to cloth diapers, which must be laundered when soiled. Many different constructions have been proposed and some have been quite successful in the market place. However, even the more successful diapers are inadequate in certain functional aspects.

One design criterion which has been sought to be achieved is the desire to keep moisture away from the surface of the diaper which comes into contact with the infant's skin and thereby avoid skin irritation and infection.

A corollary criterion to this is the desire to retain moisture in the absorbent material, i.e. once the moisture has been drawn into the absorbent material and away from the infant, it must be prevented from migrating to and concentrating at the ends of the absorbent material which are close to or, sometimes, in contact with the infant and from which the moisture can seep into the bed clothes or outer garments of the infant.

Various inventions have been directed to distributing the moisture throughout the absorbent core, and directing it to the area of the core farthest from the infant's skin, however, these embodiments have failed to prevent the migration of moisture out of the ends of the diaper. Commonly assigned Mesek et al, U.S. Pat. No. 3,612,055 discloses several diaper constructions that function extremely well in keeping moisture away from an infant's skin, while at the same time handling a full volume discharge of urine.

These functions are accomplished by a multi-layer diaper comprising, in order a fibrous facing layer which is to be brought into contact with the infant's skin, a layer of highly porous, loosely compacted cellulosic batt, a paper-like densified, highly compacted cellulosic fibrous layer integral with the loosely compacted batt, and an impervious backing sheet adhered to the densified layer throughout the interface therebetween. The facing layer is of porous construction and its fibers have less wettability for water than the fibers of the loosely compacted batt, resulting in a tendency for liquid to flow from the facing web into the batt. The densified, fibrous layer has a smaller average pore size than the loosely compacted batt, resulting in a tendency for liquid to flow preferentially from the batt into the underlying densified layer rather than to other areas of the batt, thus contending to restrict wetting in the batt to an area of moderate size. Liquid flowing into the densified layer tends to spread through the densified layer because of its wetting action, and liquid which might pass through the densified layer during discharge (when flow is rapid) is held back by the impervious backing sheet for a sufficient time to permit absorption to take place. Liquid in excess of the absorptive capacity of the densified layer is forced back by the impervious layer into the dry portion of the loosely compacted batt, thus utilizing the additional absorptive capacity therein. In the preferred species in the above-mentioned patent, the paper-like, densified layer extends continuously over substantially the entire area of the loosely compacted batt. In the continuous, paper-like, densified layer the fluid flow is outwardly from the area of initial wetting and is substantially equal in all directions.

In absorbent panels including a continuous densified layer of uniform thickness, because of the equal flow rate in all directions, it is possible for fluid to migrate to the side edges of the densified layer before it reaches the longitudinal edges thereof, with resultant flow leakage at the sides of the product. Commonly assigned Repke U.S. Ser. No. 396,242, filed Sept. 11, 1973, a continuation-in-part of Repke U.S. Ser. No. 266,013, filed June 26, 1972, which was a continuation-in-part of Repke U.S. Ser. No. 187,239, filed Oct. 7, 1971, discloses an improvement upon the diaper structures disclosed in the Mesek et al patent by providing an absorbent panel that includes a highly porous, loosely compacted fibrous cellulosic batt with an integral, continuous, paper-like, densified cellulosic fibrous layer which, in selected longitudinally aligned areas, is thickened with additional densified cellulosic fibrous material. The thickened and unthickened portions of the densified layer portion of the absorbent panel cooperate with one another to provide for increased flow of fluid within the densified portions of the absorbent structure by reason of a greater cross sectional area therein, thereby tending to cause a greater amount of the fluid passing through the facing layer and striking the loosely compacted batt portion of the absorbent panel to flow preferentially into the densified layer portion and then throughout the densified layer portion toward its outer edges.

In one embodiment of the invention, the thickened portions of the densified layer are provided by spaced, parallel strips or lines of densified fibrous material that extend lengthwise of the structure. When the absorbent panel is wetted in the central zone of the batt portion and the fluid flows into the densified layer of the absorbent panel, the thickened portions in that region function to rapidly transport the fluid lengthwise of the structure away from the initial wetted region, while the densified bridging portions between the thickened portions cause the fluid to spread laterally outwardly at a rapid rate, thus causing the fluid to encounter additional thickened portions of densified material, with resulting increased longitudinal flow.

However, in absorbent panels including a continuous, densified layer of uniform thickness and densified longitudinal lines, because of the greater flow rate in the longitudinal direction, it is possible for fluid to migrate to and be concentrated at the ends of the densified layer before it can be transferred to parallel densified lines, with resultant fluid leakage at the longtudinal edges or ends of the product. Thus, both types of absorbent panels disclosed in the above-mentioned patent and applications have certain limitations.

SUMMARY OF THE INVENTION

The present invention represents an improvement upon diaper structures as disclosed in the above-mentioned patent and applications by providing the panels thereof with width-wise densified lines near the ends of the diaper which function to divert towards the corners of the panel moisture moving toward an end edge thereof by reason of the increased lengthwise flow provided by the spaced paralleled longitudinal densified lines or by reason of initial wetting at a point close to an end of the diaper panel. The width-wise or transverse densified lines also function as the end boundaries of the densified layer and the longitudinally thickened lines, when present, i.e. the material between the ends of the diaper and the transverse lines is characterized by a porous, loosely compacted fibrous cellulosic material substantially less densified than the densified layer and thickened portions.

A method of forming improved diapers of the present invention is disclosed in commonly assigned Shepherd U.S. Patent application Ser. No. 377,372, filed July 9, 1973, and Babcock U.S. Patent application Ser. No. 377,352, filed July 9, 1973. These applications disclose apparatus which grasp a continuous web, which has been preformed with a densified layer or with a densified layer and longitudinal thickened portions, at spaced intervals, and stress and tear the web transversely to form a section. When the jaws of the apparatus of either of the above-mentioned applications are made of a hard, unyielding material, the transverse engagement and compression of the web by the jaws while the web is still lightly moistened causes a transverse densified line to be formed near the edge of each panel. The stressing of the web between the jaws of the apparatus during the tearing operation substantially eliminates, in this area, the densified layer and thickened portions, if any, thus, providing a region between the transverse, densified line and the edge of the panel which is characterized as more highly porous, more loosely compacted fibrous cellulosic material than the densified layer and longitudinal thickened portions, if any.

The transverse densified lines near the ends provide substantially greater wickability for aqueous fluid (as compared to the portions between the end and the transverse lines) and also provide for an increased volumetric flow rate of fluid in a transverse direction along the lines (as compared to the thin densified layer which terminates at the transverse line).

Fluid moving toward the end of the panel in the densified layer (with or without thickened, densified, longitudinal portions) is diverted before it reaches the end edge of the panel and caused to move sideways toward the corners. As the transverse line becomes saturated with fluid, excess fluid will tend to flow back near the side edges to previously unwetted portions of the densified layer (near the corners) in preference to flowing into the region of the panel beyond the transverse densified lines. The combination of longitudinal and transverse densified portions in the preferred embodiment thereby make possible the utilization of substantially the entire absorbant capacity of the densified layer portion, i.e., the fluid is transported to both the side edges and transverse densified lines of the batt portion of the absorbent structure, before the fluid flows into the end portions beyond the transverse densified lines or flows back into the loosely compacted batt portions of the absorbent structure.

BRIEF DESCRIPTION OF THE SEVERAL VIEWS OF THE DRAWINGS

FIG. 1 is a perspective view, with certain portions broken away of an open unfolded diaper;

FIG. 2 is a perspective view on a reduced scale of the diaper in its configuration after being put on the infant;

FIG. 3 is a plan view of an absorbent panel in a preferred embodiment of the invention;

FIG. 4 is a fragmentary, cross sectional view of the panel of FIG. 3 taken along plane 4—4, illustrating the internal structure;

FIG. 5 is a fragmentary, cross sectional view of the panel of FIG. 3 taken along plane 5—5, illustrating the internal structure;

FIG. 6 is a plan view of an absorbent panel in another embodiment of the invention;

FIG. 7 is a fragmentary cross sectional view of the panel of FIG. 6 taken along the plane 7—7, illustrating the internal structure;

FIG. 8 is a schematic view of a panel of the present invention illustrating the regions in which the transverse lines may be located;

DETAILED DESCRIPTION

Figure 9:
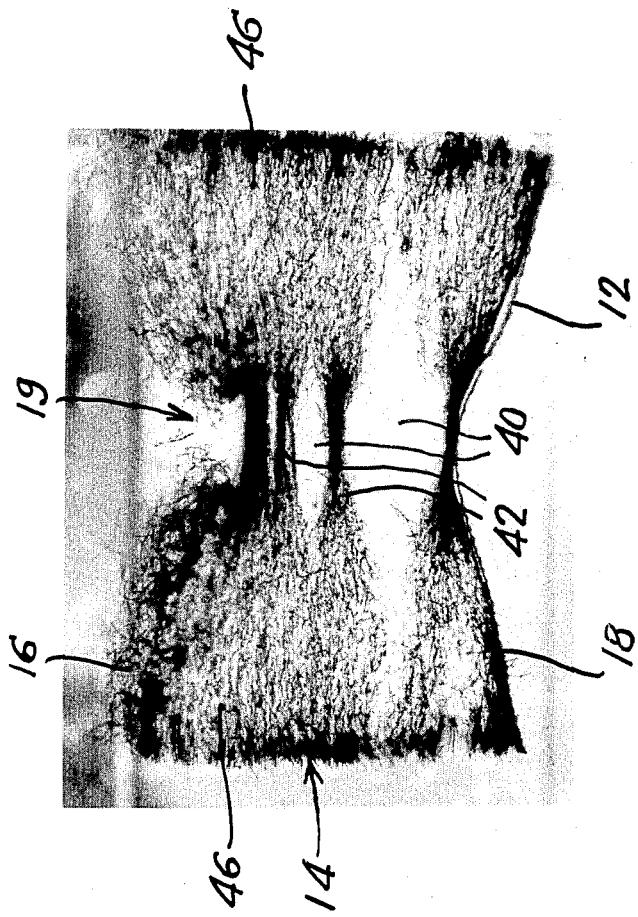
FIG. 9 is a photomicrograph of a cross section of a batt of the diaper illustrated in FIGS. 1 through 3 taken transversely to the length of a densified line.

While this invention is susceptible of embodiment in many different forms, there is shown in the drawings and will herein be described in detail a preferred embodiment of the invention and modifications thereof, with the understanding that the present disclosure is to be considered as an exemplification of the principles of the invention and is not intended to limit the invention to the embodiment illustrated. The scope of the invention will be pointed out in the appended claims.

Referring to the drawings, and particularly to FIG. 1, the diaper assembly 10, when fully opened and laid out flat, comprises a lowermost water impervious sheet 12 which is rectangular in shape, a highly water-absorbent pad, or batt 14, which is also rectangular in shape, but smaller than the impervious sheet and centrally disposed thereon, and an overlying facing layer 16 of fibrous material, which is also rectangular in shape, equal in dimension, and coterminous with the impervious sheet and in contact therewith in the marginal portions of the diaper extending peripherally beyond the absorbent batt. The batt 14 has a continuous paperlike densified highly compacted lowermost fibrous layer 18 that includes spaced, parallel, longitudinally disposed, thickened densified portons or lines 19 (FIG. 3) and transverse densified portions or lines 21. The batt 14, as illustrated in FIG. 6, may also be formed a densified layer 18 without the longitudinally disposed densified portions 19. The paper-like densified, highly compacted, fibrous layer 18 is continuous in the lowermost portion of the panel, coterminous with the sides thereof and with the transverse densified portions 21, as best illustrated in FIGS. 5 and 7. The lower major surface of the batt, including the densified layer 18, is adhered to the impervious sheet by bead lines of adhesive 22 substantially throughout the interface therebetween. Marginal portons of the facing layer 16, extending beyond the batt 14 are also adhered to the impervious sheet by adhesive bead lines 22.

In the preferred embodiment of the invention, moisture impervious sheet 12 is formed of polyethylene having a thickness of approximately 0.001 inch. The sheet may be smooth or it may be embossed to improve its drape and feel. Other suitable flexible moisture impervious sheets may be used in accordance with the invention, such as, for example, polyethylene terephthalate sheets having a thickness of about 0.0005 inches.

Batt 14 may be formed of loosely compacted short cellulosic fibers, such as wood pulp fibers, or cotton linters, or mixtures thereof, which are primarily held together by interfiber bonds requiring no added adhesive, as is known in the art. Briefly this batt is a low bulk density coherent web of loosely compacted cellulose fibers preferably comminuted wood pulp fibers in the form of so called "fluff".

The term "short fibers," as used herein, refers to fibers less than about one-fourth inch in length, in contrast to "long fibers," or "textile length fibers" which are longer than about one-fourth inch in length, and generally are between about one-half and 2½ inches in length. The former are substantially less costly than the latter. The classification of fibers by length may be carried out by the Clark Classification procedure described in the test manual or The Technical Association of Pulp and Paper Industry (TAPPI-T233 SU64).

The paper-like densified layer 18 of batt 14 is formed by a slight moistening of one surface of the batt followed by the application of pressure thereto. The nature of the batt and of its densified layer and the method of producing the same are described in U.S. Pat. No. 3,017,304, dated Jan. 16, 1972. The thickened, densified portions 19 are formed by further compression of batt 14 while it is still moist, as described in Repke, U.S. Patent applications Ser. Nos. 187,239; 266,013; and 396,242, as with embossing rollers which produce recesses on the surfaces of the batt 14 in line with the thickened portions 19. The transverse densified portions 21 may be formed by further compression of the batt 14 under suitable conditions during the severance of the batt from a continuous web while the batt is still moist and is contacted by hard edged jaws, as described in Shepherd Ser. No. 377,372 and Babcock Ser. No. 377,352. An alternative apparatus of forming densified portions 21 would utilize a roller having transverse embossments to compress the batt after the densified layer 18 or densified layer 18 and longitudinal portions 19 had been formed. However, this latter apparatus is not preferred due to the problem of timing the web with the tearing apparatus which severs the batt 14 from the continuous web.

The composite density of batt 14, including its densified layer 18, should be above about 0.07 gm./cc. and preferably between about 0.10 and 0.15 gm./cc. The foregoing density values are applicable to the diaper as produced. In storage and handling, the loft or thickness of the batt is increased to some extent, resulting in lowered densities.

In the embodiment of FIGS. 1 and 2, facing layer 16 is made up of a mixture of fibers consisting predominantly of short cellulosic fibers such as wood pulp fibers or cotton linters, in amounts of about 75% to about 98%, the balance being textile length fibers such as rayon. Short cellulosic fibers such as wood pulp fibers or cotton linters are substantially less expensive than textile length cellulosic fibers such as cotton and rayon, and this low cost is a factor in reducing the cost of the facing layer component of the diaper of this invention.

In the facing layer, the short fibers are in uniform admixture with 2% to 25% by weight of textile length fibers, such as 1.5 denier rayon fibers uniformly cut to 1½ inch length. The short and long fibers are randomly and substantially uniformly dispersed and bonded with a bonding agent such as a self-cross-linking acrylic emulsion. The facing web is also treated with a wetting agent to partially counteract the water-repellency of the bonding agent and bring the facing layer to the desired degree of wettability. Facing layers of this character are described in greater detail in commonly-owned Liloia et al. U.S. Pat. No. 3,663,348.

Facing layers suitable for use in this invention have fabric weights in the range of 1 to 5 oz./yd.$^2$ and densities less than 0.15 gm./cc., generally in the range between 0.05 and 0.1 gm./cc. The dry strength of the facing layer for a fabric having a weight of about 1.5 oz./yd.$^2$, is at least 0.15 lbs/in. of width in the machine direction and at least 0.10 lbs/in. of width in the cross direction. The fabrics have unusually good elongation, loft, softness and drape characteristics in comparison to prior products incorporating any substantial amount of short fibers.

An important aspect of this invention is the provision for selective wettability among the above-described fibrous components of the diaper, such that the moisture is selectively drawn from the facing layer into the body of the batt and then from the body of the batt into the densified layer thereof.

The least wettable of the fibrous elements of the diaper of this invention is facing layer 16. However, even in the facing layer the ability to be wetted by water is desired. Water repellency in the facing layer is not desired since, at the desired fiber densities in the facing layer, water repellency can prevent the liquid from penetrating into the facing layer and the absorbent layers behind it, just as a tent fabric holds back penetration of rain water. For this reason, the facing layer is usually treated with a wetting agent, such as an anionic surfactant, to moderate and reduce the water repellency which may be imparted to the short and long fibers of the web by the bonding agent which bonds them into an integral layer. After treatment with a wetting agent, the facing layer is receptive to penetration by urine but remains less wettable than the batt.

The body of batt 14 is substantially more wettable than the facing layer and tends to draw liquid away from the facing layer. The individual fibers of the batt are extremely wettable, generally having liquid-fiber contact angles below about 15° and approaching zero in the optimum embodiment, as described in detail in the above-mentioned application. The wickability, or preferential absorptivity of the body of the batt for water is limited, however, by its low density which results in a large effective capillary radius for the capillaries between adjacent fibers.

The pressure causing a liquid to enter a cylindrical capillary is expressed by the equation:

$$P = \frac{2 \gamma \cos O}{r}$$

wherein P is the capillary pressure,
  $\gamma$ is the surface tension of the liquid,
  O is the liquid-fiber contact angle, and
  r is the capillary radius.

With a given liquid, the pressure (capillary force) increases with the cosine of the liquid-fiber contact angle (reaching a maximum where the angle is zero), and decreases with narrower capillary radii so that narrower capillaries will draw liquid from wider ones.

The relative wickability between facing layer 16 and the body of batt 14 is affected by both the relative densities of the layers and the relative wettability of the individual fibers in each layer. The facing layer is sometimes more dense than the body of the batt, tending to provide greater wickability in the facing layer, but even then the individual fibers of the batt have substantially smaller liquid-fiber contact angles than those of the facing layer, overcoming the density difference and providing a substantial overall increase in capillary pressure to absorb liquid into the body of the batt.

Densified fiber layer 18 of the batt provides the maximum capillary pressure because it combines the very low contact angle of the fibers of the batt with the high density (small capillary radius) of the densified fibers.

When urine is voided into an area in facing layer 16, it partially wets the facing layer and is absorbed therein, spreading out to a limited extent to form a roughly circular wetted zone therein. When the urine passes through the facing layer and comes into contact with the body of batt 14, it is preferentially absorbed into the body of the batt because of the enhanced wettability thereof. It spreads within the body of the batt to wet a roughly circular zone therein that is slightly larger than the wetted zone in facing layer 16. When the urine passes through the body of the batt it initially contacts one or more of the thickened densified portions 19 (in the preferred species) and the urine is strongly drawn into the densified layer 18 because of its high density and is spread laterally through a much larger zone, or to the edges of the batt, depending on the amount of urine passed. The urine is transported rapidly along lines 19, more rapidly than it is transported transversely across the densified bridging portions between the lines, with the result that the roughly circular zone in the initially wetted loosely compacted portion of the batt is distorted into a roughly oval zone in the densified portion of the batt.

The urine is transported relatively rapidly in all directions of the densified layer 18 because the densified layer is continuous over the area defined by the transverse lines 21 and sides of the absorbent panel. However, the thickened portions 19 provide for an increased volumetric flow rate in the longitudinal direction to rapidly move a larger volume toward the ends of the absorbent structure. When the volume of urine is quite large, the liquid may travel longitudinally along one of the lines 19 until it encounters one of the transverse densified lines 21. Densified lines 21 then transfer the flow to adjacent lines 19 and toward the corners of the batt in preference to transfer into the undensified end portions between lines 21 and the end edges and thus help avoid leakage of fluid at the end edges of the batt.

On occasions when a substantial amount of urine has been voided, transverse lines 21 becomes actuated and all portions of the densified layer become saturated and excess urine must then pass into the previously dry portions of the body of the batt including its end portions. It is to be noted, however, the such flow does not take place until substantially all of the densified portions of the batt have utilized their entire absorptive capacities.

The diaper of this invention is normally packaged and sold in a folded condition as described in the above mentioned U.S. Pat. No. 3,017,304. Briefly, the side margins of the impervious sheet 12 and the facing web 16, together with a portion of batt 14, are folded inwardly in a first fold to provide as the uppermost layer of the fold, a portion of the moisture impervious sheet. This sub-assembly is then folded outwardly along each edge in a second fold to cover the first folded portion and to expose the edge portion of the facing web as the upper layer of the double fold. In the preferred embodiment, each double fold at the edge of the diaper comprises approximately one-third of the resulting transverse dimension of the folded diaper, leaving approximately one-third of the width of the folded diaper as a central unfolded and uncovered portion.

The diaper is held in its folded condition by two small central spots of adhesive applied between the main body of the diaper and the overlying sides of the facing web 16, one spot on each folded side of the diaper. When the diaper is to be put on the infant, the folds are opened on one side of each of the adhesive spots, and the open portion of the diaper is put under the infant's buttocks while the folded portion is raised into the crotch region. The final form of the diaper is shown in perspective on a reduced scale in FIG. 2. In one form of the invention, as illustrated in FIG. 2, the diaper is provided with adhesive tabs 26, each having a fixed end secured to the impervious sheet 12 and a free end wherein the adhesive surface is covered with a facing sheet. The facing sheets are removed to expose the adhesive surfaces when the diaper is applied to the infant, as in the configuration shown in FIG. 2, and the free ends of the adhesive tabs 26 are secured to opposite corners of the diaper.

Suitable fibrous structures for making the pads or batts 14 used in this invention are made from short cellulosic fibers obtained by the grinding or comminution of compacted wood pulp fibers or cotton linters. When the thickened densified portions extend through a substantial portion of the cross sectional thickness of batt 14, or completely through the cross sectional thickness to the side of the batt opposite the side having the continuous densified portion, the batt is strengthened.

The batts are initially formed by air blowing the cellulosic fibers onto a support at a total weight of about 2 to about 10 oz./yd.$^2$, and then subjecting the air blown fibers to heavy compression. The small amount of moisture which may, when required, be added to cellulosic pulpboard is uniformly distributed throughout the air blown fibers by the grinding and air blowing operations, and after compression, this moisture provides weak hydrogen bonding to give some integrity to the body of the batt.

The dense compacted paper-like layer 18 or skin is prepared by moistening a surface of the cellulosic batt with a fine spray of water, and then subjecting the moistened batt to pressure. The formation of the densified skin on the cellulosic batt is believed to be due to the formation of strong hydrogen bonds between contacting moistened fibers, similar to the bonds between the fibers in paper. By the proper selection of the amount of the amount of moisture applied to the surface of the batt and by the proper selection of degree of compression imposed, the properties of the densified skin may be varied as desired. The thickness, density, strength and other characteristics of the densified skin will depend upon the uniformity by which the moisture is applied, the depth to which it penetrates, and the degree to which the fibers are compressed. For example, by finely spraying about 0.0015 cc. of water per square centimeter of web surface and then exposing the web to a pressure of about 40 pounds per square inch, a suitable densified, coherent paper-like skin 18 is obtained on the surface of the web which has been moistened. The thickened densified portions 19 may be obtained by subjecting the web to additional pressure, as by the use of an embossing roll, while the web is still moist, and the additional pressure is preferably several times higher than the pressure that is applied to form the densified layer 18. The densified lines 21 may be obtained by subjecting the web to still further pressure, as by the use of an embossing roll, while the web is still wet. However, the preferred method of forming densified lines 21 is by compression of the fibers during the severance of a section of batt 14 from the continuous web from which it is formed. The pressure required in forming the densified lines 21 in either manner is preferably several times higher than the pressure that is applied to form the densified layer 18. By changing the pressure used in forming the thickened portions 19 and densified portions 21, the extension of these portions into the cross sectional thickness of the batt 14 may be controlled. In the illustrated embodiments, these portions 19 and 21 extend entirely through the cross section of the batt, FIGS. 4, 5 and 7. As will be observed in FIGS. 4, 5 and 7, the portions 19 and 21 merge smoothly with the densified layer 18.

It should be noted that there is a definite density gradient within the densified portions 19 and 21. Due to the compressibility of the fibers in these portions, the pressure applied to form the densified layer is attenuated from the points of contact on the batt surfaces, i.e. the densified layer 18 on one side and the fluff on the other side, at increasing distances in the cross section of the batt. As a result, the density of the densified portions 19 and 21 is greatest at the interface with densified layer 18 and gradually decreases and blends with the surrounding fluff.

Figure 10:
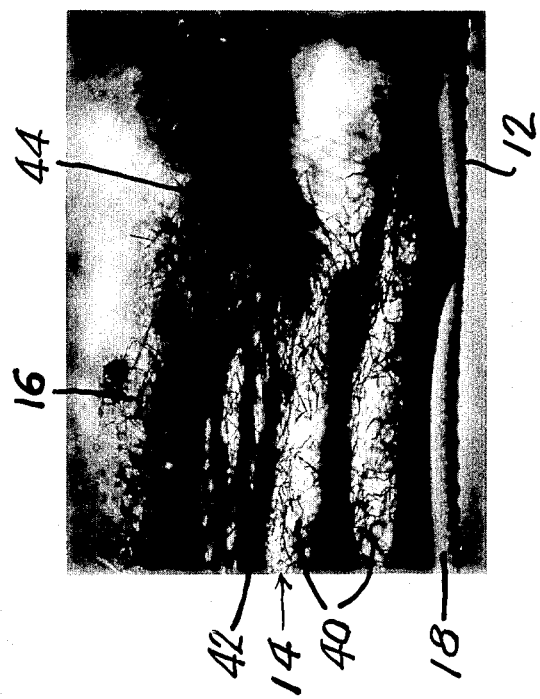
FIG. 10 is a photomicrograph of a batt as illustrated in FIG. 9 and taken in the direction of a densified line.

The terms "thickened lines" or "thickened portions", as used herein, are intended to refer to limited areas (as compared to the total area of the fibrous batt structure) in which at least some of the fibers above the continuous densified skin are more closely compacted than the fibers above the continuous densified skin in other areas of the fibrous batt structure, and the terms thickened lines or thickened portions apply to both the coherent or unitary structures and to structures having voids, pores, or gaps therein as shown in FIGS. 9 and 10. Within the areas designated as thickened lines or thickened portions, the densities (whether calculated on the basis of total volumes within these areas or on the basis of the volumes of the compacted portions without the voids) are higher than the density in other portions of the fibrous batt structure above the continuous densified skin. the thickened lines or thickened portions as defined above can extend completely or partially through the cross-sectional thickness of the fibrous batt structure, it being understood that the amount of thickening is dependent upon the extent to which it is desired to rapidly transport fluid away from an initially wetted area and the degree to which it is desired to reinforce the fibrous batt structure.

With specific reference to FIGS. 9 and 10, the disposable diaper illustrated in cross section therein is generally of the type shown in FIGS. 1–3, and includes facing layer 16, batt 14, and backing sheet 12 which is attached to the batt. Batt 14 includes a loosely compacted cellulosic fibrous portion at the side thereof adjacent the facing layer, and integral therewith on the opposite side, a continuous paper-like densified, cellulosic fibrous layer 18.

Batt 14 is subjected to embossing pressure subsequent to the formation of the densified layer or skin 18 by a ribbed embossing roll to form a plurality of spaced, parallel thickened densified portions or lines 19. The densified portions 19 are not coherent and unitary and instead, the moisture application and embossing forces are coordinated and controlled so that densified portions 19 having substantially fiber-free regions 40 therein, which may be termed "voids", "pores", "cells", "gaps", or "pockets". The longitudinally disposed densified portions 19 and the transverse densified portions 21 are similar in cross section, and FIGS. 9 and 10 are applicable to both densified portions 19 and 21.

As is evident by comparing FIGS. 9 and 10, densified portions 19 and 21 include a plurality of vertically spaced fiber-free regions 40 which are generally lens-shaped in transverse cross section (FIG. 9) and which are elongated in the direction of the densified portions (FIG. 10). The regions 40 are separated from one another by spaced fibrous strata 42 which are generally parallel with one another and with the opposite major faces of the batt 14, as can be best seen in FIG. 10. The strata 42 are of random or non-uniform length and merge together (and with the continuous densified layer 18) at longitudinally spaced locations 44 to completely enclose regions 40. As is also evident from FIGS. 9 and 10, regions 40 are of non-uniform cross-sectional dimension and length.

While it is not intended to be limited to any particular theory, it is believed that under certain selected moisture and pressure conditions (which may vary for different pulp fibers), as the batt dries subsequent to the embossing step, the hydrogen bonds which may have previously caused the lines to be cohesive or unitary begin to weaken due to the inherent recovery force of the fibrous mass, which cause the lins to separate as shown in FIGS. 9 and 10.

Batts such as known in FIGS. 9 and 10 may also be produced by mechanically working a product having coherent or unitary lines, as by subjecting the product to bending and/or twisting forces, which cause certain of the hydrogen bonds to rupture, thus producing a product having thickened lines with dense fibrous strata surrounding substantially fiber-free regions.

While each of the strata 42 may have a density that is greater than the fibrous regions 46 at opposite sides of the densified portions 19 and 21, the density of the strata 42 is not necessarily uniform and the strata in the mid-portion of the batt may be less dense than the strata outwardly thereof.

It will be appreciated that with thickened densified portions or lines having separated planes or strata of densified material, fluid will flow in the direction of the lines at a rapid linear rate, although the volumetric flow rate within each of the planes of densified material will, of necessity, be low because of the limited cross-sectional area in each plane. However, the voids or pores between the planes of densified material act as reservoirs into which excess liquid carried in the planes can be spilled, thereby providing an increased volumetric storage capacity and an increased volumetric carrying capacity, as compared to a cohesive or unitary line containing the same total amount of fibers.

The short fibers used in making batt 14 of this invention are generally entirely fibers of wood pulp or cotton liners. However, other cellulosic fibers may be used as well as blends of cellulose fibers with other fibers such as silk, wood, nylon, and cellulose acetate. Highly purified kraft paper pulp fibers have proven to be most satisfactory for most applications.

The facing layer, as described above, contains between 75% and 98% by weight of short fibers, not exceeding about one-fourth inch in length. The average short fibers are from about one-sixteenth to about three-sixteenth inch in length. The facing layer is prepared by first forming a web of randomly laid dry fibers of the desired mix of short and long lengths, the web having a density from about 0.09 gm./cc. to about 0.025 gm./cc. measured by ASTM Method D-1777 at 0.16 lbs./in.$^2$ Facing layers, as described above, having weights between about 1 and about 5 ounces per square yard are generally suitable for use in this invention. One particular facing layer which has been used with satisfaction is composed of approximately 15% textile-length fibers such as uniformly cut one and one-half inch 1.5 denier rayon fibers and 85% fibers of individualized second cut cotton linters. This facing layer is made on a web laying device to a weight of 2 oz./yd.$^2$ This layer is then conveyed into a bonder including a suction means, and a bonding agent such as a self-cross-linking acrylic emulsion is applied. One bonding agent which has been employed with considerable success is a latex of a polyethyl-acrylate copolymer containing small amounts of acrylonitrile and a cross-linkage monomer sold under the trademark HYCAR 2600 × 120. The bonding agent should preferably be of the low viscosity type with a viscosity less than 5 centipoises.

To avoid excessive water repellency, a surfactant, preferably an anionic surfactant, is included in the binder suspension. A typical surfactant which has been found to be suitable is the ionic sulfonated alkyl ester sold under the trademark TRITON GR-5.

The composition of the binder suspension and the amount of suction at the suction slot is controlled in a typical application so as to give the fabric a dry solids add-on of 6% based on the fabric weight, of which about 0.15% is the amount of surfactant. A suitable range for the amount of binder is from about 4½% to about 9%, based on fabric weight.

The wet web is conveyed into a drying oven having a temperature of 310°-320°F., where it is dried and the resin binder cured. The resultant material has a density of 0.05 to 0.07 gm./cc., and a dry strength of about 1.4 lbs./in. of width in the cross direction. The wet strengths are about 0.09 lbs./in. of width in the machine direction and about 0.5 lbs./in. of width in the cross direction.

The bonding agent in the facing layer tends to provide a layer with greater dimensional stability than the body of the batt which contains no bonding agent. When the diaper is wet with urine and the infant's weight is on a portion thereof, both the facing layer and the body of the batt will be compressed under the weight, but the body of the batt is more subject to compression because it contains no bonding agent. This increased compaction in the body of the batt enhances the margin of wickability which it normally has in comparison to the facing layer (even when dry and uncompressed) and tends to hold the liquid strongly against migration into the facing layer where it could wet the infant's skin.

If desired, the facing layer may be made with a veneer of long fibers on one or both surfaces thereof, in place of or in addition to the long fibers intermixed with the short fibers.

In another embodiment, the facing layer may be made substantially entirely of textile length fibers bonded together with a resinous bonding agent. This embodiment can provide a facing layer of greater strength, but it is not preferred because it is more expensive and because the strength of the short fiber-containing facing material is adequate in most instances.

In all embodiments of the invention, the adherence of the impervious layer to the densified layer, continuously or discontinuously, over substantially the entire interface between them is important because it prevents substantial separation between the two and the creation of substantial spaces in which substantial amounts of free liquid urine can accumulate. The adherence of the impervious layer to the paper-like densified cellulosic layer effects a dimensional stabilization of the densified layer against transverse movement and thereby brings about a stabilization of the loosely compacted fiber fluff portion of the batt layer since the paper-like densified layer is integral with the fluff portion of the batt, and holding forces are transmitted from the dimensionally stable impervious layer through the widely distributed adhesive, to the densified layer, and thence to the fluff.

Turning now to the positioning of the transverse densified lines 21, the batt structure, FIG. 8, illustrates the regions wherein the transverse lines 21 may be located to provide efficient use of the absorbent characteristics of the batt. Dotted line 30 is the transverse median of the batt and dotted lines 31 are spaced at distances of one half the width of the batt from the median. The region 32, defined by lines 31 and the ends of the batt, are suitable for locating the transverse densified lines 21. In the batt structure illustrated in FIG. 6, only a densified layer 18 and transverse lines 21 have been formed. In this type of batt structure the liquid flow rate within the densified layer will be equal in all directions. Thus, the transverse lines 21 must be spaced from the median 30 at least a distance of one half the width of the batt 14. This minimum spacing assures that urine, which is generally deposited at the central portion of the batt 14 through facing layer 16, will not reach one border of the densified layer 18 before it reaches the other borders, i.e., the sides and transverse densified lines 21. This same minimum spacing may be used with batt structure utilizing longitudinal thickened portions 19, FIG. 3. However, the minimum spacing is not preferred in this type of structure, since the thickened portions produce greater liquid flow rates in the longitudinal direction. Therefore, in batt structures utilizing longitudinal thickened portions 19, the transverse densified lines 21 should be positioned at even greater distances from the transverse median, which are consistent with the desired design criterion, i.e. minimum liquid concentration at the ends of the batt. When the batt is severed from a continuous web under suitable conditions, with hard edged jaws contacting the batt as disclosed in the above-mentioned Shepherd and Babcock applications, the transverse lines are positioned close to the ends of the diaper, these positions being desirable for optimum use of the absorbent characteristics of the batt.

As discussed above, the transverse lines 21 form the end borders for the densified layer 18 and longitudinal lines 19, if any. These borders assure that the bounded region of the batt will become saturated, due to the distribution characteristics of the densified layer and density gradient boundary of the transverse lines 21, before liquid will migrate into the regions beyond the transverse lines 21.

It will be appreciated from FIG. 7 that where a series of transverse lines 21 are used, the boundary effect will be greatly enhanced. Serially arranged densified lines 21 present even greater flow barriers than a single line.

It will be understood by those skilled in the art that variations and modifications of the specific embodiments described above may be employed without departing from the scope of the invention as defined in the appended claims.

We claim:

1. A multi-layer diaper comprising: a porous facing layer; a highly porous, loosely compacted, cellulosic fibrous batt of greater lengths than width in face-to-face juxtaposition to said facing layer and having greater wettability to water than said facing layer; a paper-like, densified compacted cellulosic fibrous layer of relatively high wettability and relatively high fluid retentivity integral with said loosely compacted batt on the face thereof opposite the face in juxtaposition to said facing layer; said densified compacted fibrous layer being thickened in selected linear regions across the width of said batt and near the ends thereof to direct the flow of fluid to selected areas of said densified layer; said densified layer extending continuously over substantially the entire area of said batt except for the region between the ends and said selected regions, and a water impervious backing sheet adhered to said densified layer.

2. The diaper of claim 1 wherein said densified layer has thickened portions in longitudinal linear areas.

3. The diaper of claim 1 wherein said densified layer is of a substantially uniform thickness on said face of the batt except for said selected linear regions.

4. The diaper of claim 1 wherein said selected linear regions are provided by a single densified line near each end of the batt.

5. The diaper of claim 1 wherein said selected linear regions are provided by a plurality of spaced parallel lines near each end of the batt.

6. A multi-layer diaper comprising: a porous facing layer in the form of a water-wettable bonded web of mixed long and short fibers; a highly porous, loosely compacted, cellulosic fibrous batt in face-to-face juxtaposition to said facing layer; a paper-like, densified compacted cellulosic fibrous layer of relatively high wettability and relatively high fluid retentivity integral with said loosely compacted batt on the face thereof opposite the face in juxtaposition to said facing layer; said densified layer extending continuously over a given area of said batt and being thickened longitudinally in selected regions to increase the fluid handling capacity of the densified layer and to direct the flow of fluid to selected areas of the densified layer, said layer being transversely thickened in selected end regions to direct flow of fluid to selected regions of said densified layer, and a water-impervious backing sheet adhered to said densified layer.

7. The diaper of claim 6 wherein said densified layer is of generally uniform thickness throughout a major portion of said given area and merges with said loosely compacted batt at a generally planar interface.

8. The diaper of claim 7 wherein the thickened portions of said densified layer extend beyond the plane of the interface between said batt and the densified layer and into said batt.

9. The diaper of claim 8 wherein the outer face of said densified layer includes recesses in alignment with said thickened portions.

10. The diaper of claim 8 wherein the longitudinally thickened portions of said densified layer are defined by relatively narrow zones spaced from and parallel with one another and extending from the transverse thickened regions at one end to the transverse thickened regions at the other end of said batt.

11. The diaper of claim 10 wherein said densified layer extends continuously over one side of said loosely compacted batt from the transverse thickened regions at one end to the transverse thickened regions at the other end of said batt, and the portions of said batt between the ends thereof and the transverse thickened regions are substantially less densified than said densified layer.

12. The diaper of claim 6 wherein said transverse thickened regions are located in the batt at distances of at least one half of the width of the batt from the transverse median thereof.

13. The diaper of claim 6 wherein said selected transverse thickened regions extend through a major portion of the cross sectional thickness of the batt.

14. The diaper of claim 6 wherein said selected transverse thickened regions extend through the entire cross sectional thickness of the batt.

15. The diaper of claim 6 wherein said selected transverse thickened regions are provided by a plurality of spaced parallel lines.

16. The diaper of claim 6 wherein said selected transverse thickened regions are provided by the thickened line near each end of the batt.

17. A multi-layer diaper comprising: a porous facing layer in the form of a water-wettable bonded web of mixed long and short fibers, of which from about 75 to about 98 weight percent are short fibers having a fiber length less than one-fourth inch and from about 2 to about 25 weight percent are long fibers having a fiber length between about one-half and about 2½ inches, said fibers being bonded together by a water repellent bonding agent and coated with a surfactant; a highly porous, loosely compacted, cellulosic fibrous batt in face-to-face juxtaposition to said facing layer and having greater wettability to water than said facing layer; a paper-like, densified compacted cellulosic fibrous layer of relatively high wettability and relatively high fluid retentivity integral with said loosely compacted batt on the face thereof opposite the face in juxtaposition to said facing layer, said densified layer extending continuously over a given area of said batt and being of generally uniform thickness throughout a major portions of said given area, said densified layer merging with said batt at a generally planar interface and including longitudinal portions thicker than said major portions and extending beyond the plane of the interface and into said batt; said densified layer and thickened portions being bordered in the lengthwise direction by transverse thickened linear portions in said batt, and a water-impervious backing sheet adhered to said densified layer by an adhesive discontinuously distributed over the entire interface between them, said backing sheet and facing layer being substantially rectangular and substantially coextensive and said batt being substantially rectangular, narrower than said backing sheet and facing layer and centrally disposed with respect thereto to provide marginal portions of said diaper in which said backing sheet and said facing layer are in direct contact with each other.

* * * * *

UNITED STATES PATENT AND TRADEMARK OFFICE
CERTIFICATE OF CORRECTION

PATENT NO. : 3,965,904
DATED : June 29, 1976
INVENTOR(S) : Frederick K. Mesek and Virginia L. Repke It is certified that error appears in the above-identified patent and that said Letters Patent are hereby corrected as shown below:

In Column 4, line 42, "portons" should read --- portions ---.

In Column 4, line 44, "formed a" should read --- formed with a ---.

In Column 4, line 54, "portons" should read ---- portions ----.

In Column 9, line 48, "skin. the" should read --- skin. The ---.

In Column 10, line 34, "lins" should read --- lines ---.

In Column 10, line 36, "as known in" should read --- as shown in ---.

Signed and Sealed this

Twenty-sixth Day of April 1977

[SEAL]

Attest:

RUTH C. MASON
*Attesting Officer*

C. MARSHALL DANN
*Commissioner of Patents and Trademarks*